(12) United States Patent
Panov et al.

(10) Patent No.: US 7,282,612 B2
(45) Date of Patent: *Oct. 16, 2007

(54) METHOD FOR PRODUCING MONOCYCLIC KETONES $C_4$-$C_5$

(75) Inventors: Gennady Ivanovich Panov, Novosibirsk (RU); Konstantin Alexandrovich Dubkov, Novosibirsk (RU); Evgeny Vladimirovich Starokon, Novosibirsk (RU); Larisa Vladimirovna Pirutko, Novosibirsk (RU)

(73) Assignee: Institut Kataliza Imeni G.K. Boreskova Sibirskogo Otdelenia Rossiliskoi Akademii Nauk, Novosibirsk (RU)

( * ) Notice: Subject to any disclaimer, the term of this patent is extended or adjusted under 35 U.S.C. 154(b) by 0 days.

This patent is subject to a terminal disclaimer.

(21) Appl. No.: 10/508,367

(22) PCT Filed: Nov. 6, 2002

(86) PCT No.: PCT/RU02/00493

§ 371 (c)(1),
(2), (4) Date: Jul. 14, 2005

(87) PCT Pub. No.: WO03/078372

PCT Pub. Date: Sep. 25, 2003

(65) Prior Publication Data

US 2006/0106258 A1    May 18, 2006

(30) Foreign Application Priority Data

Mar. 20, 2002   (RU) .............................. 2002106986

(51) Int. Cl.
*C07C 49/00* (2006.01)

(52) U.S. Cl. ................................... 568/375

(58) Field of Classification Search .................... None
See application file for complete search history.

(56) References Cited

U.S. PATENT DOCUMENTS

| | | | |
|---|---|---|---|
| 2,223,494 A | 12/1940 | Loder | |
| 2,371,794 A | 3/1945 | Boyd | |
| 2,377,412 A | 6/1945 | Frey | |
| 4,745,228 A | 5/1988 | Decker et al. | |
| 4,806,692 A | 2/1989 | Yamada et al. | |
| 5,856,581 A | 1/1999 | Alas et al. | |

FOREIGN PATENT DOCUMENTS

| | | |
|---|---|---|
| GB | 649680 | 1/1951 |
| SU | 504749 A | 6/1976 |

OTHER PUBLICATIONS

Bridson-Jones et al., Oxidation of Organic Compounds by Nitrous Oxide, In J.Chem.Soc., Nov. 1951; pp. 2999, 3001, 3004, 3008.
Pannetier, G., et al. "Regions of flammability of binary mixtures of hydrocarbons with nitrous oxide: action of nitrous oxide as oxidant" *Fifth Symposium on Combustion* (1995) pp. 620-628.
Brandt, B.B., et al. "Firing limites for $N^2O$ mixtures with inflammable gases and vapours" *Khimicheskaya Promyshlennost* (1960) No. 5, pp. 67-73.
Partial English translation of Brandt, B.B., et al. "Firing limites for $N^2O$ mixtures with inflammable gases and vapours" *Khimicheskaya Promyshlennost* (1960) No. 5, from p. 69-72.

*Primary Examiner*—Sikarl A. Witherspoon
(74) *Attorney, Agent, or Firm*—Ladas and Parry LLP

(57) ABSTRACT

The invention relates to a method for producing monocyclic ketones $C_4$-$C_5$. The inventive method is based on the reaction of a liquid-phase oxidation of monocyclic alkenes $C_4$-$C_5$ into corresponding cyclic ketones by nitrogen oxide or the mixture thereof with an inert gas. The process is carried out at a temperature ranging from 20 to 300° C. and a pressure of nitrogen oxide ranging from 0,01 to 100 atm. The inventive process ensures the high selectivity with respect to target products, the explosion safety at work and is promising for industrial use.

18 Claims, No Drawings

METHOD FOR PRODUCING MONOCYCLIC KETONES $C_4$-$C_5$

This is application is a 371 of PCT/RU02/00493, filed Nov. 6, 2002, and published as WO 03/078372 on Sep. 25, 2003.

FIELD OF THE INVENTION

The present invention relates to a method for producing monocyclic ketones $C_4$-$C_5$ and more particularly to a method for producing thereof by liquid-phase oxidation of corresponding liquid alkenes using nitrous oxide ($N_2O$).

Cyclic ketones are valuable intermediate products in the synthesis of various organic compounds. For instance, cyclopentanone is used for synthesizing δ-valerolactone, ghlutaric acid, as well as sebacic acid, which is used for producing Nylon-6,10. Cyclopentanone is also used as a solvent.

BACKGROUND OF THE INVENTION

There are known several methods for producing lower cyclic ketones. For example, according to U.S. Pat. No. 2,223,494, C07C 29/50, 1940, cyclopentanone and cyclobutanone are produced by the oxidation of cyclopentane and cyclobutane, respectively, with air oxygen. The reaction is carried out at 120-170° C., using Co, Mn, Cu, Ce salts as a catalyst. This method is disadvantageous in that a large amount of cyclic alcohol is formed along with the ketone, and in that selectivity drops sharply as the conversion increases.

Cyclopentanone can also be produced by catalytic dehydrogenation of cyclopentanol in the gaseous phase at 250-375° C. over a Cu—Zn catalyst [U.S. Pat. No. 2,377,412, C07C 45/00, 1945] or at 160-250° C. over a Ni catalyst [U.S. Pat. No. 2,371,794, C07C 5/05, 1945]. Practical application of this method involves difficulties in view of the absence of cheap sources of cyclopentanol.

A method is known for producing cyclopentanone from adipic acid [U.S. Pat. No. 5,856,581, C07C 45/48, 1999] or esters thereof [U.S. Pat. No. 4,745,228, C07C 45/48, 1988] in the presence of oxide catalysts. Apart from high cost of the feed stock, the first method is disadvantageous in the necessity of carrying out the process in an aggressive acid medium at a high temperature (200-300° C.). In the case of using esters, an additional step of preparing the latter is required, the process flowsheet becoming thus complicated.

According to U.S. Pat. No. 4,806,692, C07C 45/34, 1989, cyclopentanones can also be produced by the oxidation of cyclopentene in the liquid phase with air oxygen, using a homogeneous catalyst $PdCl_2$—$CuCl_2$ at a temperature of up to 80° C. This method is disadvantageous in a low efficiency of the process and the necessity of using aggressive HCl solution.

In GB Pat. No. 649680, C07C 45/34, 1951 there is claimed a process for the oxidation of olefins into carbonyl compounds with nitrous oxide. According to this process, in particular, it is possible to produce cyclopentanone by oxidizing cyclopentene. This process is disadvantageous in a low efficiency and severe reaction conditions.

A second serious disadvantage of this process is the possibility of flammable mixtures to be formed. In order to rule out explosion hazards, the authors of said GB Patent propose to introduce additionally saturated hydrocarbons into the reaction mixture.

However, as later investigations have shown, mixtures of saturated hydrocarbons with $N_2O$ are almost as explosion-hazardous, as mixtures of olefins. Thus, limit concentrations of propylene in $N_2O$ are 1.8 to 26.8%, and limit concentrations of propane are 2.1 to 24.8% [G. Panetier, A. Sicard, V Symposium on Combustion, 620 (1995); B. B. Brandt, L. A. Matov, A. I. Rozlovsky, V. S. Khailov, Khim. Prom., 1960, No. 5, pp. 67-73 (in Russian)]. Therefore saturated hydrocarbons, in spite of their smaller reactivity, cannot serve as a means for ruling out explosion hazards.

SUMMARY OF THE INVENTION

The present invention protects a method for producing cyclobutanone and cyclopentanone by oxidizing cyclic alkenes $C_4H_6$ and $C_5H_8$, this method being free of the above-indicated disadvantages. For example, in the case of cyclopentene the reaction proceeds according to the following equation:

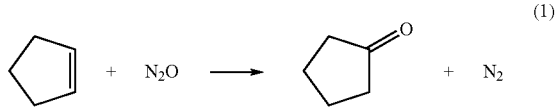

(1)

According to this method, for enhancing selectivity, the reaction is carried out under milder conditions, when cycloalkenes are present in the form of a liquid phase, wherein the reaction proceeds with a high selectivity. Excessive increase of the $N_2O$ temperature and/or pressure is undesirable, because it may lead to lowering the selectivity owing to contribution made by the gas phase oxidation.

Explosion-safe operation conditions according to the proposed method are provided by adding an inert gas which does not react with $N_2O$, for instance, nitrogen, argon, helium, carbon dioxide gas, etc., or a mixture thereof, to the reaction mixture. Effluent gases of the reaction can play the role of an inert gas. In different steps of the process, depending on the "cycloalkene:nitrous oxide" ratio, the proportion of an inert gas, required for ensuring explosion-safe operation, can be different and be provided by supplying such gas separately. From the standpoint of simplicity and maximum safety of the process, it is expedient to have such dilution of nitrous oxide with an inert gas that the reaction mixture should be not explosion-hazardous at any content of cycloalkene. This condition is fulfilled, if the content of $N_2O$ in the mixture with an inert gas is not greater than 25%. The use of such a mixture rules out the origination of explosion-hazardous situations in all the steps of the process.

For decreasing explosion-hazardousness, burning inhibitors, such as trifluorobromomethane, difluorochlorobromomethane, dibromotetrafluoroethane and others, can be added to the reaction mixture.

In accordance with the present invention, the oxidation of monocyclic alkenes $C_4$-$C_5$ into cyclic ketones can be carried out within a wide range of conditions both in a static and in a flow reactor which can be manufactured from steel, titanium, glass, or any other suitable material. All known techniques increasing the efficiency of gas-liquid reactions can be employed in this case.

In the case of a static variant, cycloalkene is introduced into a n autoclave (without a solvent or with a solvent) in such amount that upon heating to the temperature of the reaction cycloalkene should be present in the form of liquid phase. Then nitrous oxide or its mixture with an inert gas is supplied, the pressure being brought to a preset value. The amount of nitrous oxide is selected such that its pressure at the reaction temperature should be 0.01 to 100 atm. After that the reactor is heated to the reaction temperature within a range of 20 to 300° C. The reaction time is selected depending on the conditions under which the reaction is carried out, as well as on the requirements to be met by the process, and may vary from several minutes to several tens of hours.

The reaction of oxidation of cycloalkenes $C_4$-$C_5$ can be carried out either without a solvent or with a solvent which can be selected from a wide range of substances conventionally employed in the practice of organic synthesis. The reaction proceeds with a sufficiently high rate without a catalyst. However, it can be conducted also with the use of a catalyst.

The proposed method for producing cyclic ketones does not require high purity of the starting reagents. Thus, nitrous oxide can be used both in pure form and in admixtures of various gases which do not affect adversely the reaction characteristics. Cycloalkenes $C_4$-$C_5$ may also contain admixtures of various organic compounds, especially if they do not contain double bonds C=C.

The essence of the proposed invention is illustrated by the following Examples.

EXAMPLES 1-5

These Examples (Table 1) demonstrate high selectivity of the liquid-phase oxidation reaction with the help of nitrous oxide.

Example 1. 33 cm³ of cyclopentene (Aldrich, 99%) are poured into a 100 cm³ reactor made from stainless steel and provided with a stirrer (Parr Co.). The reactor is purged with nitrous oxide, and then the pressure of nitrous oxide is brought to 10 atm. The reactor is heated to 197° C. and maintained at this temperature during 5 hrs. On completion of the reaction, the reactor is cooled down to room temperature, the pressure is measured, and the final composition of the gaseous and liquid phases is analyzed by gas chromatography and chromatography-mass spectrometry techniques. From the obtained data the conversion of cyclopentene and the selectivity of the reaction for cyclopentanone are calculated;

$$X = \frac{C_{CyON} + \sum C_{side}}{C_{CyEN}^0} \cdot 100(\%) \quad (2)$$

$$S = \frac{C_{CyON}}{C_{CyON} + \sum C_{side}} \cdot 100(\%), \quad (3)$$

where $C_{CyEN}^0$ is the initial cyclopentene concentration; $C_{CyON}$ is the cyclopentene concentration in reaction products; $\Sigma C_{side}$ is the total concentration of by-products. In the case of large conversions, the value X can be calculated also from the difference between the initial and final concentrations of cyclopentene:

$$X = \frac{C_{CyEN}^0 - C_{CyEN}}{C_{CyEN}^0} \cdot 100(\%) \quad (4)$$

Example 2 is similar to Example 1, the difference being in that the reaction is carried out at 195° C. during 12 hours.

Example 3 is similar to Example 2, the difference being in that the reaction is carried out at a temperature of 150° C.

Example 4 is similar to Example 3, the difference being in that the reaction is carried out at 175° C. during 10 hours.

Example 5 is similar to Example 4, the difference being in that the reaction is carried out at 225° C. during 3 hours.

TABLE 1

| Example | T (° C.) | Time (hrs) | X (%) | S (%) |
|---|---|---|---|---|
| 1 | 197 | 5 | 7.7 | 98 |
| 2 | 195 | 12 | 15.6 | 97 |
| 3 | 150 | 12 | 3.5 | 97.5 |
| 4 | 175 | 10 | 8.5 | 98 |
| 5 | 225 | 3 | 13 | 99 |

EXAMPLE 6

This Example is a comparative one. The experiment is carried out as in Example 1, the difference being in that the reactor is charged with 5 ml of cyclopentene. With such charging under the reaction conditions the whole of the cyclopentene is in the gaseous phase. As a result of the experiment, the conversion of cyclopentene was approximately 0.5%. This result indicates that under the abovesaid conditions the reaction in the gas phase practically does not go.

EXAMPLES 7-8

These Examples, as compared with Example 1, demonstrate the influence of the nitrous oxide concentration on the process characteristics (Table 2). The nitrous oxide concentration in the reaction mixture is preset by the value of its initial pressure at room temperature, $P_{N_2O}^0$.

Example 7 is similar to Example 1, the difference being in that the initial pressure of nitrous oxide at room temperature in this experiment is set to be equal to 25 atm.

Example 8 is similar to Example 1, the difference being in that the initial pressure of nitrous oxide in this experiment is set to be equal to 5 atm.

TABLE 2

| Example | $P_{N_2O}^0$ (atm) | T ° C.) | X (%) | S (%) |
|---|---|---|---|---|
| 1 | 10 | 197 | 7.7 | 98 |
| 7 | 25 | 197 | 20.5 | 99 |
| 8 | 5 | 197 | 4.0 | 98 |

EXAMPLES 9-10

Examples 9-10 (Table 3) demonstrate the possibility of carrying out the process in the presence of a catalyst.

Example 9 is similar to Example 1, the difference being in that the reaction is carried out in the presence of 0.15 g of $Fe_2O_3/SiO_2$ (2.8 wt. % of $Fe_2O_3$). The catalyst is prepared by impregnating $SiO_2$ with a solution of $FeCl_3$, dried at 110° C. and calcined in air at 500° C. for 2 hrs.

Example 10 is similar to Example 1, the difference being in that the reaction is carried out in the presence of 0.5 g of $Ag/SiO_2$ (1 wt. % of Ag). The catalyst is prepared by impregnating $SiO_2$ with a solution of $AgNO_3$, dried at 110° C. and calcined in air at 500° C. for 2 hrs.

TABLE 3

| Example | Catalyst | T (° C.) | X (%) | S (%) |
| --- | --- | --- | --- | --- |
| 9 | $Fe_2O_3/SiO_2$ | 197 | 7.5 | 97.5 |
| 10 | $Ag/SiO_2$ | 197 | 8 | 97 |

EXAMPLES 11-14

These Examples demonstrate the possibility of cyclopentene oxidation in the presence of a solvent (Table 4).

Example 11 is similar to Example 1, the difference being in that 10 ml of cyclopentene and 75 ml of isobutanol are poured into the reactor.

Example 12 is similar to Example 1, the difference being in that 10 ml of cyclopentene and 50 ml of cyclohexane are poured into the reactor.

Example 13 is similar to Example 3, the difference being in that 10 ml of cyclopentene and 50 ml of acetonitrile are poured into the reactor.

Example 14 is similar to Example 13, the difference being in that instead of acetonitrile use is made of heptane and the reaction is carried out at 220° C. for 5 hrs.

TABLE 4

| Example | Solvent | T (° C.) | X (%) | S (%) |
| --- | --- | --- | --- | --- |
| 11 | Isobutanol | 195 | 15.6 | 98 |
| 12 | Cyclohexane | 195 | 12.6 | 98 |
| 13 | Acetonitrile | 150 | 2.5 | 97.5 |
| 14 | Heptane | 220 | 32.2 | 99.0 |

EXAMPLES 15-20

Examples 15-20 (Table 5) demonstrate the possibility of carrying out the reaction with diluted mixtures of nitrous oxide.

Example 15 is similar to Example 7, the difference being in that instead of pure nitrous oxide its mixture with an inert gas—nitrogen is fed to the reactor, in which mixture the concentration of $N_2O$ is 70% The initial pressure of the mixture in the reactor ($P^0$) is set to be 49 atm.

Example 16 is similar to Example 15, the difference being in that the concentration of $N_2O$ in the mixture with nitrogen is 20%.

Example 17 is similar to Example 16, the difference being in that the initial pressure in the reactor is set to be 98 atm. The reaction is carried out at 195° C. for 12 hours.

Example 18 is similar to Example 15, the difference being in that the concentration of nitrous oxide is 50%, and the initial pressure of the mixture of $N_2O$ and $N_2$ is set to be 32 atm. The reaction is carried out at 225° C. for 3 hours.

Example 19 is similar to Example 17, the difference being in that instead of nitrogen argon is used, in which the concentration of nitrous oxide is 40%. The initial pressure of the mixture of $N_2O$ and Ar is set to be 43 atm.

Example 20 is similar to Example 19, the difference being in that carbon dioxide gas is used instead of argon.

TABLE 5

| Example | Inert gas | $P^0$ (atm) | Concentration of $N_2O$ in mixture (%) | T (° C.) | Time (hrs) | X (%) | S (%) |
| --- | --- | --- | --- | --- | --- | --- | --- |
| 15 | $N_2$ | 49 | 70 | 197 | 5 | 22.0 | 98 |
| 16 | $N_2$ | 49 | 20 | 197 | 5 | 4.0 | 98 |
| 17 | $N_2$ | 98 | 20 | 195 | 12 | 15.0 | 97 |
| 18 | $N_2$ | 32 | 50 | 225 | 3 | 14.0 | 99 |
| 19 | Ar | 43 | 40 | 195 | 12 | 16.2 | 99 |
| 20 | $CO_2$ | 43 | 40 | 195 | 12 | 15.8 | 98 |

Examples 15-20 demonstrate that cyclopentene is oxidized with a high selectivity into cyclopentanone with the aid of nitrous oxide diluted with an inert gas. The content of nitrous oxide in a mixture with an inert gas can be varied in a wide range, including the range of $N_2O$ concentrations of 25% and less, in which the possibility of explosion hazardous situations is ruled out in any compositions with cycloalkene $C_4$-$C_5$. As Examples 16-17 demonstrate, the oxidation of cycloalkenes in this range proceeds with a high efficiency.

In the present invention there is proposed a new method for producing cyclic ketones $C_4$-$C_5$, based on the reaction of liquid-phase oxidation of cyclic alkenes $C_4H_5$ and $C_5H_8$ with nitrous oxide or a mixture thereof with an inert gas. The process provides high selectivity, explosion safety and is promising for industrial application.

The invention claimed is:

1. A method for producing monocyclic ketones $C_4$-$C_5$, carried out by contacting a liquid cycloalkene with nitrous oxide at a temperature of 20 to 300° C. and a pressure of nitrous oxide of 0.01 to 100 atm in the presence of a diluent inert gas.

2. A method according to claim 1, wherein the concentration of an inert gas in the reaction mixture does not exceed 99%.

3. A method according to claim 1, wherein the concentration of an inert gas is selected such as to rule out the possibility of explosion-hazardous compositions to be formed in each step of the process.

4. A method according to claim 1, wherein the concentration of an inert gas is selected such as to rule out the possibility of explosion-hazardous compositions to be formed in all steps of the process.

5. A method according to claim 1, wherein the reaction is carried out at a temperature of 20 to 199° C. and a pressure of nitrous oxide of 0.01 to 100 atm without introducing an inert gas into the reaction mixture.

6. A method according to claim 1, wherein the reaction is carried out in the presence of a catalyst.

7. A method according to claim 1, wherein the reaction is carried out in the presence of a solvent.

8. A method according to claim 1, wherein nitrous oxide contains admixtures of other gases which do not impair the process characteristics.

9. A method according to claim 1, wherein the reaction is carried out in a static or flow reactor.

10. A method according to claim 1, wherein recirculating gases are used for carrying out the reaction.

11. A method according to claim 2, wherein the concentration of an inert gas is selected such as to rule out the possibility of explosion-hazardous compositions to be formed in each step of the process.

12. A method according to claim 2, wherein the concentration of an inert gas is selected such as to rule out the possibility of explosion-hazardous compositions to be formed in all steps of the process.

13. A method according to claim 2, wherein the reaction is carried out in the presence of a catalyst.

14. A method according to claim 2, wherein the reaction is carried out in the presence of a solvent.

15. A method according to claim 2, wherein nitrous oxide contains admixtures of other gases which do not impair the process characteristics.

16. A method according to claim 2, wherein the reaction is carried out in a static or flow reactor.

17. A method according to claim 2, wherein recirculating gases are used for carrying out the reaction.

18. A method according to claim 4, wherein the reaction is carried out in the presence of a catalyst.

* * * * *